United States Patent
Ferguson (10) Patent No.: US 10,634,330 B1
(45) Date of Patent: Apr. 28, 2020

(54) HEADBAND ASSEMBLY

(71) Applicant: RIVERPOINT MEDICAL, LLC, Portland, OR (US)

(72) Inventor: John Thomas Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 70 days.

(21) Appl. No.: 15/799,100

(22) Filed: Oct. 31, 2017

(51) Int. Cl.
*F21V 23/02* (2006.01)
*F21V 23/04* (2006.01)
*F21V 23/00* (2015.01)
*F21L 4/04* (2006.01)
*A61B 90/35* (2016.01)
*F21V 21/30* (2006.01)
*A61B 90/50* (2016.01)
*F21W 131/20* (2006.01)

(52) U.S. Cl.
CPC ............ *F21V 23/02* (2013.01); *A61B 90/35* (2016.02); *F21L 4/04* (2013.01); *F21V 21/30* (2013.01); *F21V 23/002* (2013.01); *F21V 23/0414* (2013.01); *F21V 23/0485* (2013.01); *A61B 2090/502* (2016.02); *F21W 2131/20* (2013.01)

(58) Field of Classification Search
CPC ........ F21V 23/02; F21V 21/30; F21V 23/002; F21V 23/0414; F21V 23/0485; F21V 33/0004; F21V 33/0068; A61B 90/35; A61B 2090/502; F21L 4/04; F21W 2131/20
See application file for complete search history.

(56) References Cited

U.S. PATENT DOCUMENTS

| 3,008,040 A | 11/1961 | Moore |
| 3,704,928 A | 12/1972 | Coombs et al. |
| D228,474 S | 9/1973 | Barber |

(Continued)

FOREIGN PATENT DOCUMENTS

| EP | 2479489 A2 | 7/2012 |
| KR | 1020110095674 A1 | 8/2011 |

(Continued)

OTHER PUBLICATIONS

MEDLED, medLED Sapphire O.R. Surgical Headlight System, brochure, medLED//Portable Surgical Lighting, Portland, Oregon United States of America.

*Primary Examiner* — Bao Q Truong
(74) *Attorney, Agent, or Firm* — Timothy E. Siegel Patent Law, PLLC; Timothy E. Siegel (57) ABSTRACT

A medical headlamp assembly, including a headlamp subassembly and a headstrap subassembly, that has a headstrap having an interior surface that touches the user's head when the headstrap is being worn. Battery holders are supported by the headstrap away from the headstrap interior surface, so that batteries held by the battery holders have no interior surface that is closer than 2 mm away from the headstrap interior surface, and thereby, away from the user's head. Also, battery contacts are positioned to be contacted by batteries held in the battery holders. Finally, an electrical network is electrically connected to the battery contacts and a headlamp subassembly connector, physically connected to the headlamp subassembly and electrically connects the headlamp subassembly to the electrical network.

7 Claims, 5 Drawing Sheets

(56) References Cited

U.S. PATENT DOCUMENTS

| | | | |
|---|---|---|---|
| 3,830,230 | A | 8/1974 | Chester |
| 4,516,190 | A | 5/1985 | Kloots |
| 4,916,579 | A | 4/1990 | Simms |
| 5,068,771 | A | 11/1991 | Savage |
| 5,667,291 | A | 9/1997 | Caplan |
| 5,760,546 | A | 6/1998 | Pabla |
| 5,774,271 | A | 6/1998 | Lagerway |
| 5,926,320 | A | 7/1999 | Parkyn, Jr. et al. |
| 6,033,087 | A | 3/2000 | Shozo |
| 6,566,816 | B2 | 5/2003 | Fushimi |
| 6,601,966 | B1 | 8/2003 | Wiklund |
| 6,841,950 | B1 | 1/2005 | Walker |
| RE39,162 | E | 7/2006 | Caplan |
| 7,210,810 | B1 | 5/2007 | Iversen et al. |
| 7,226,185 | B2 | 6/2007 | Dolgin |
| 7,671,544 | B2 | 3/2010 | Clark |
| 7,737,194 | B2 | 6/2010 | Kashiwagi et al. |
| 7,762,698 | B2 | 7/2010 | Menze |
| 7,780,313 | B2 | 8/2010 | Lam |
| 7,847,302 | B2 | 12/2010 | Basin et al. |
| 8,337,036 | B2 | 12/2012 | Soto et al. |
| 8,436,542 | B2 | 5/2013 | Middleton-White |
| 8,449,132 | B2 | 5/2013 | Lau |
| 8,587,213 | B2 | 11/2013 | Yee |
| 9,091,428 | B2 | 7/2015 | Ferguson |
| 9,234,653 | B2 | 1/2016 | Ferguson |
| 9,351,799 | B2 | 5/2016 | Ferguson |
| 9,568,177 | B2 | 2/2017 | Ferguson |
| 9,761,847 | B2 | 9/2017 | Chen et al. |
| 2003/0224247 | A1 | 12/2003 | Wheeler |
| 2005/0099824 | A1 | 5/2005 | Dowling et al. |
| 2005/0117327 | A1 | 6/2005 | Gupta |
| 2005/0243558 | A1 | 11/2005 | Van Duyn |
| 2006/0098440 | A1 | 5/2006 | Allen |
| 2006/0285316 | A1 | 12/2006 | Tufenkjian et al. |
| 2007/0097703 | A1 | 5/2007 | Goldfain |
| 2008/0130272 | A1 | 6/2008 | Waters |
| 2008/0144306 | A1 | 6/2008 | Medinis |
| 2008/0285259 | A1 | 11/2008 | Uke |
| 2008/0316733 | A1* | 12/2008 | Spartano ............... F21L 14/00 362/105 |
| 2009/0168414 | A1 | 7/2009 | Bailey |
| 2009/0207617 | A1 | 8/2009 | Merchant et al. |
| 2010/0091491 | A1 | 4/2010 | Jiang et al. |
| 2010/0110695 | A1 | 5/2010 | Nakamura |
| 2010/0277894 | A1* | 11/2010 | Kim ..................... F21L 4/00 362/105 |
| 2010/0313335 | A1 | 12/2010 | Water |
| 2011/0026258 | A1 | 2/2011 | Chang |
| 2012/0014113 | A1 | 1/2012 | Chen |
| 2012/0120635 | A1* | 5/2012 | Strong ................ F21V 21/084 362/105 |
| 2012/0120636 | A1 | 5/2012 | Wilt et al. |
| 2012/0175025 | A1 | 8/2012 | Gerolemou |
| 2013/0128586 | A1 | 5/2013 | Lim |
| 2013/0197317 | A1 | 8/2013 | Daniel et al. |
| 2013/0328074 | A1 | 12/2013 | Lowes |
| 2014/0291715 | A1 | 10/2014 | Reiherzer et al. |
| 2014/0334132 | A1 | 11/2014 | Ferguson |
| 2014/0334157 | A1 | 11/2014 | Ferguson |
| 2014/0334159 | A1 | 11/2014 | Ferguson |
| 2016/0123563 | A1 | 5/2016 | Ferguson |
| 2016/0207228 | A1 | 7/2016 | Ferguson |
| 2017/0301906 | A1 | 10/2017 | Adamson et al. |

FOREIGN PATENT DOCUMENTS

| | | |
|---|---|---|
| WO | 2009063224 A2 | 5/2009 |
| WO | 2010144426 A1 | 12/2010 |

* cited by examiner

HEADBAND ASSEMBLY

BACKGROUND

To a surgeon performing a lengthy operation, the comfort of a headlamp assembly can be a significant issue. Even a small area of discomfort can become increasingly unpleasant, as the hours pass. Moreover, for headlamp assemblies which hold the batteries on the headband, it is necessary for the headband to include an electric network that permits a user to adjust the brightness of the headlamp, without wasting very much electric power. This function is typically performed by a DC-to-DC convertor, in the form of a switching regulator. The placement of a circuit card hosting this network has been problematic, adding to the potential for hard pressure-spot on the side of the head.

Another problem encountered in the use of headbands is a tendency for the linkage to the headlamp to sway, as the wearer moves his head. This creates an irritating movement of the light spot.

Another issue that arises in the use of headlamp assemblies is diagnosing assembly failure. There has been an issue in models in which the electronics are buried in the headband, of finding where in the circuitry the failure has occurred. Simply isolating the failure to headlamp (sometimes referred to as "bezel"), or the circuitry held within the headband portion can prove daunting.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a medical headlamp assembly, comprising a headstrap subassembly adapted to fit in a preferred orientation on a human wearer's head, and including a battery and a conductor extending from the battery to a front-center position, relative to the wearer's head when the headstrap is in the preferred orientation. A headlamp subassembly is connected to and supported by the headstrap subassembly at the front center position, including a headlamp and a linkage, connected to the front center position and supporting the headlamp. Also, a user input mechanism permits a user to indicate a desired brightness from the headlamp and a circuit board, positioned at the front center position of the headstrap subassembly, being no greater than 5 cm in width, and electrically connected to the conductor and to the headlamp, and including an integrated circuit implementing a DC-to-DC convertor supplying power to the headlamp, from the conductor, the power varying in accordance with the user input mechanism.

In a second separate aspect, the present invention may take the form of a medical headlamp assembly, including a physical unit, including a headstrap subassembly and a headlamp subassembly connected to and supported by the headstrap subassembly, including a headlamp and a linkage, connecting the headlamp to the headband. Also, an electrical network permits a controllable brightness level to be produced by the headlamp, and includes a motion detection element attached to the physical unit and is configured so that a first predetermined movement of the physical unit causes an increase in the controllable brightness level of the headlamp and a second predetermined movement of the physical unit causes a decrease in the controllable brightness level of the headlamp.

In a third separate aspect, the present invention may take the form of a medical headlamp assembly, including a headlamp subassembly and a headstrap subassembly, that has a headstrap having an interior surface that touches the user's head when the headstrap is being worn. Battery holders are supported by the headstrap away from the headstrap interior surface, so that batteries held by the battery holders have no interior surface that is closer than 2 mm away from the headstrap interior surface, and thereby, away from the user's head. Also, battery contacts are positioned to be contacted by batteries held in the battery holders. Finally, an electrical network is electrically connected to the battery contacts and a headlamp subassembly connector, physically connected to the headlamp subassembly and electrically connects the headlamp subassembly to the electrical network.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
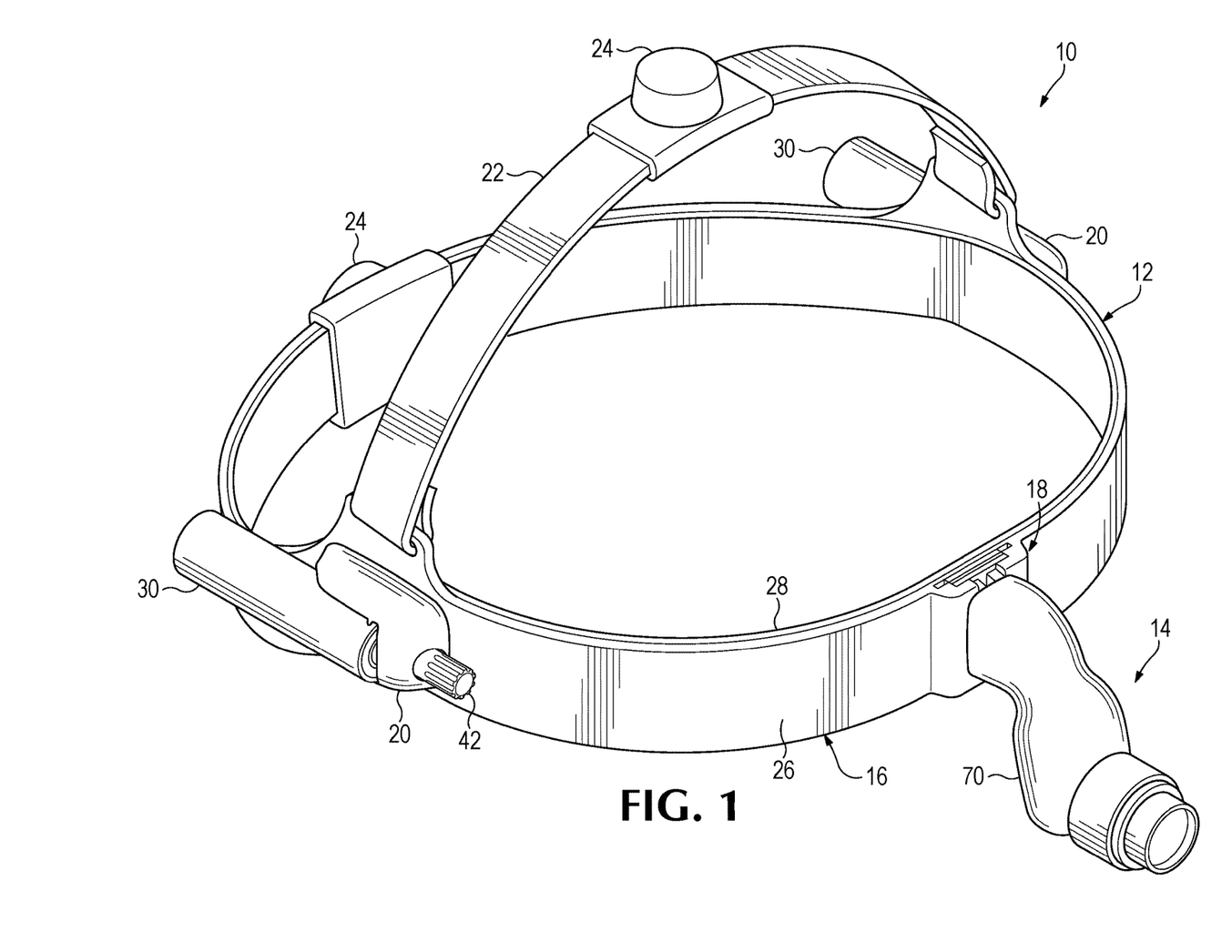
FIG. 1 is an isometric view of a medical headlamp assembly, according to the present invention.
Figure 2:
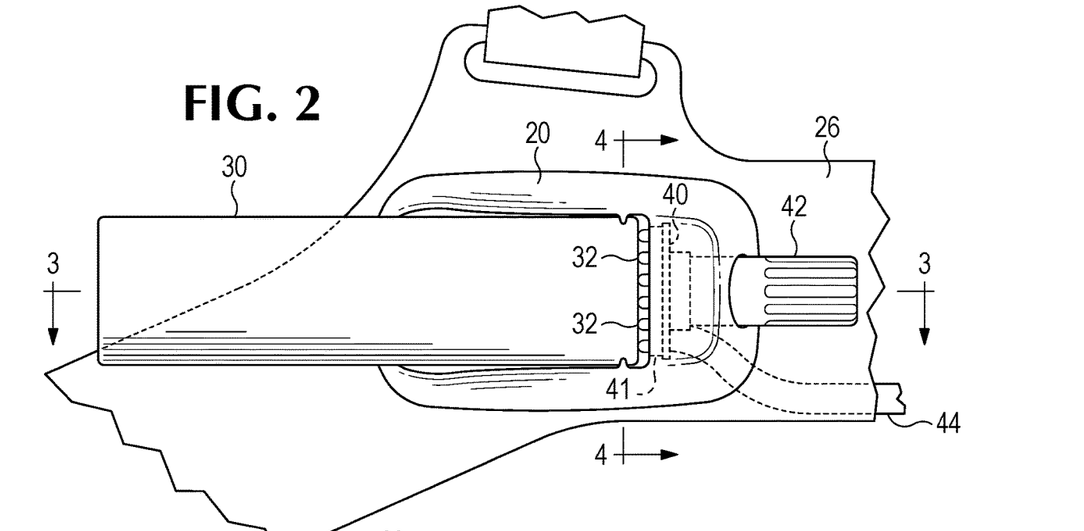
FIG. 2 is a side view of a battery holder that forms a part of the medical headlamp assembly of FIG. 1.

In a preferred embodiment of a medical headlamp assembly 10, according to the present invention, a headstrap sub-assembly 12 supports a headlamp sub-assembly 14. The headstrap sub-assembly 12 is made up of a headstrap 16, a headlamp sub-assembly connector 18, battery holders 20, a top strap 22, and tightening mechanisms 24. A pair of batteries 30, each having a circular set of battery contacts 31, are fit into battery holders 20.

In a preferred embodiment, as shown, headstrap 16 is formed of an outer layer 26 and an inner layer 28. Outer layer 26 is formed of a continuous piece of molded plastic, that goes all the way around the user's head. Not only does this design simplify the manufacturing process, but it eliminates possible discomfort points formed where one piece of material is connected with another. The top strap 22 can be disengaged from headstrap 16, by way of snaps (not shown) where the top strap reconnects with itself after being threaded through the slots in the headstrap 16, or by some other means. In an alternative embodiment, top strap 22 has no fastener 24, to loosen or tighten, but has some elasticity, to stretch to the desired length. Both types of top straps 22 may be supplied to the user at time of purchase, in a user kit.

Figure 4:
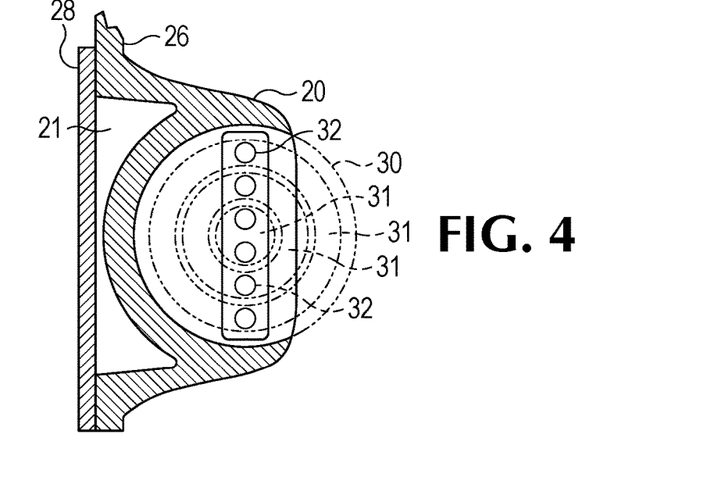
FIG. 4 is a forward-looking view of the battery holder, taken along lines 4-4 of FIG. 2.

As shown in FIG. 4, battery holder 20 is formed so that there is a gap 21 between itself and inner layer 28. This adds to wearer comfort as batteries 30, are hard and nonyielding relative to material used in headstrap 16. In previous designs, after many hours of wear, batteries 30 have been known to cause quite a bit of discomfort to a wearer, such as a surgeon. By holding each battery 30, so that it is displaced from the headstrap 16, the battery does not press against the wearer's head. A set of battery contacts 32, press against the contacts of the battery 31, which are circular and include both anode and cathode on the same lengthwise end of the battery. Two contacts 32, touch each one of contacts 31, to produce a robust electrical connection. The use of magnets, modern manufacturing techniques with low tolerance for nonuniformity and the redundant use of contacts 32 permits the elimination of springs used to urge mating contacts into good electrical connection. Such springs, very common in the use of battery connections, are a frequent failure point in prior art systems. Also, because contacts 31 are symmetric and on just one lengthwise side of batteries 30, the placement of batteries 30 into holders 20 does not require any effort to correctly orient batteries 30, other than to verify that the side with the clearly visible contacts 31 faces contacts 32. In prior art systems, some extra time may be necessitated to rotate the batteries into the correct position, before sliding them into the battery holders. Assembly 10 is designed so that the batteries 30 can be replaced sequentially ("hot swapped"), so that there is never a moment when assembly 10 is deprived of battery power and stops emitting light. In a high-pressure surgical operation, any extra complication in this procedure is undesirable. In an additional advantage, batteries 30 extend outwardly lengthwise from holders 20, by more than 1 cm, making batteries 30 easy to grasp and remove by the person performing the hot swap. In a preferred embodiment, batteries 30 extend lengthwise from battery holders 20 by more than 4 cm. In an additional preferred embodiment, batteries 30 extend lengthwise from battery holders 20 by more than 6 cm.

In additional preferred embodiments, batteries 30 are not round cylinders, but are cylinders that are square in cross-section. In this embodiment the contacts are not circular, but have quadrilateral symmetry, so that any way that the battery would fit into the square cross-section battery holders would cause the battery contacts to align to form a good connection. In yet another embodiment, the batteries are in the form of non-square rectangle in cross-section, with the contacts having bi-lateral symmetry, so that any of the two ways in which the batteries could fit into the battery holders having a matching shape, would result in a good contact. In one embodiment, the batteries have terminals at both lengthwise ends, but only one lengthwise end needs to make contact with battery holder contacts to form a circuit, with both polarities connected in the circuit.

Battery holders 20 may be formed as part of outer layer 26, during an injection molding process. The inner, face contacting layer 28 is later adhered to layer 26, to provide greater wearer comfort. Although gap 21 is shown as a simple void, in an alternative embodiment it is filled with a foam, or similar material. In an alternative embodiment, the volume 21 is filled with the same polymer that makes up the rest of outer layer 26. Although this may result in slightly more pressure against a wearer's head, it is only over an area of about 0.7 cm×1 cm, and it is still less pressure than prior art headlamp assemblies placed against the wearer's head.

Figure 3:
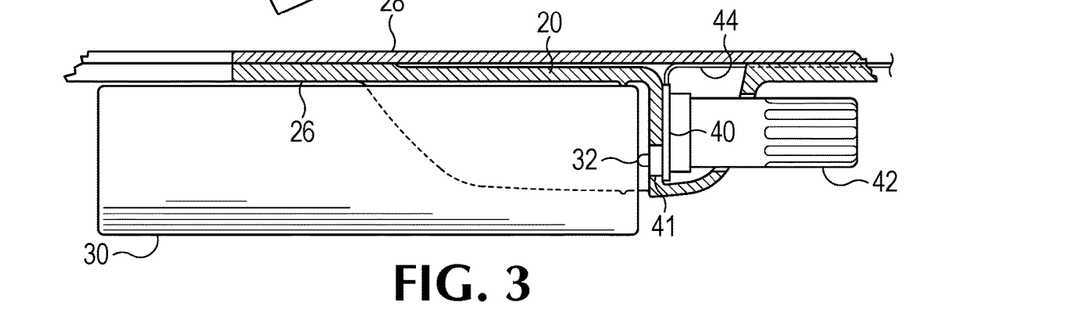
FIG. 3 is a top view of the battery holder of FIG. 2, taken along lines 3-3 of FIG. 2.

Referring to FIG. 3, a structure that includes a printed circuit board (PCB) 40, connected to battery contacts 32 by way of a contact supporting panel 41, and a brightness control knob 42 is inserted into each holder 20. The PCB 40 extends in a direction perpendicular to the wearer's head, so that as a new battery 30 is introduced into holder 20 it does not press against a contact that in turn presses against the head of the wearer. Also, the PCB 40 itself must be hard, so with this design the hard PCT does not cause a discomfort area on the wearer's head.

A flex circuit 44 (alternatively a ribbon cable) is connected to printed circuit board 40, electrically connecting it to a centrally located circuit board 60 (FIG. 7), described below. In embodiments, inner layer 28 is much thinner than outer layer 26, or even nonexistent, with flex circuit 44 simply adhered into a linear indentation. In embodiments, battery holder 20 is in the form of a wing, extending backward and having its rearmost extent free from contact with strap 16. Batteries 30 include magnetic material, the circuit board 40, or the panel 41, or both (depending on the embodiment) includes mating magnetic material, to help attract battery 30 into a robust mating contact with contacts 32 and to assist in the retention of batteries 30, after they have been put in. In a preferred embodiment, battery holders 20 hold batteries 30, so that no portion of batteries 30 come closer than within 2 mm of the interior surface (that is the surface that touches the head) of headstrap 16. Further, there is preferably an air gap 21 (FIG. 4) or a gap filled with foam or other deformable material, between each battery 30 and the interior surface of strap 16 (and therefore the head of the user). This arrangement greatly increases wearer comfort by essentially eliminating pressure on the head from the batteries 30. The cylindrical design of batteries eases the design task, relative to a battery having a large flat surface facing the head. In one embodiment, batteries 30 expand outwardly, in a step, on the portion extending outward of holders 20. In another embodiment, the batteries are similar to batteries 30, but are a straight round cylinder.

Figure 5:
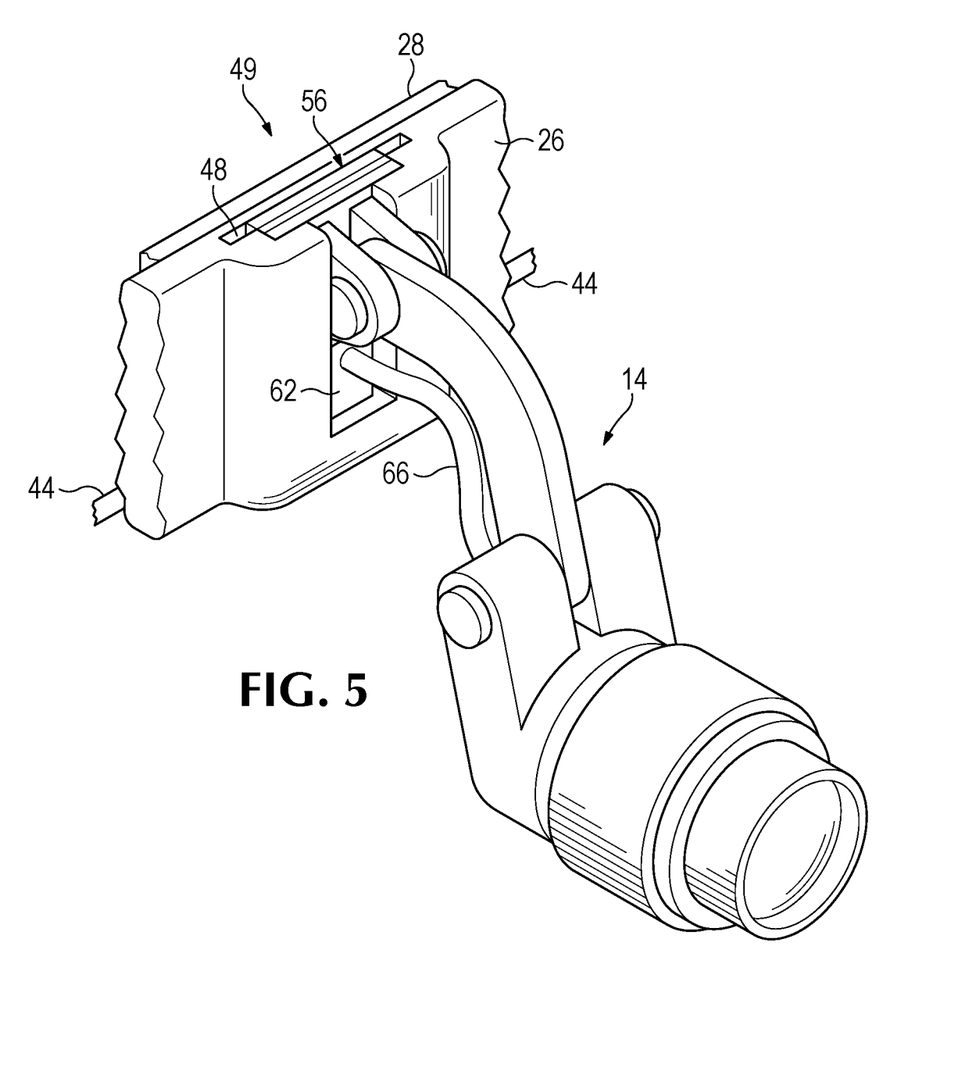
FIG. 5 is an isometric detail view of the headlamp and headband connection area, of the headlamp assembly of FIG. 1.
Figure 6:
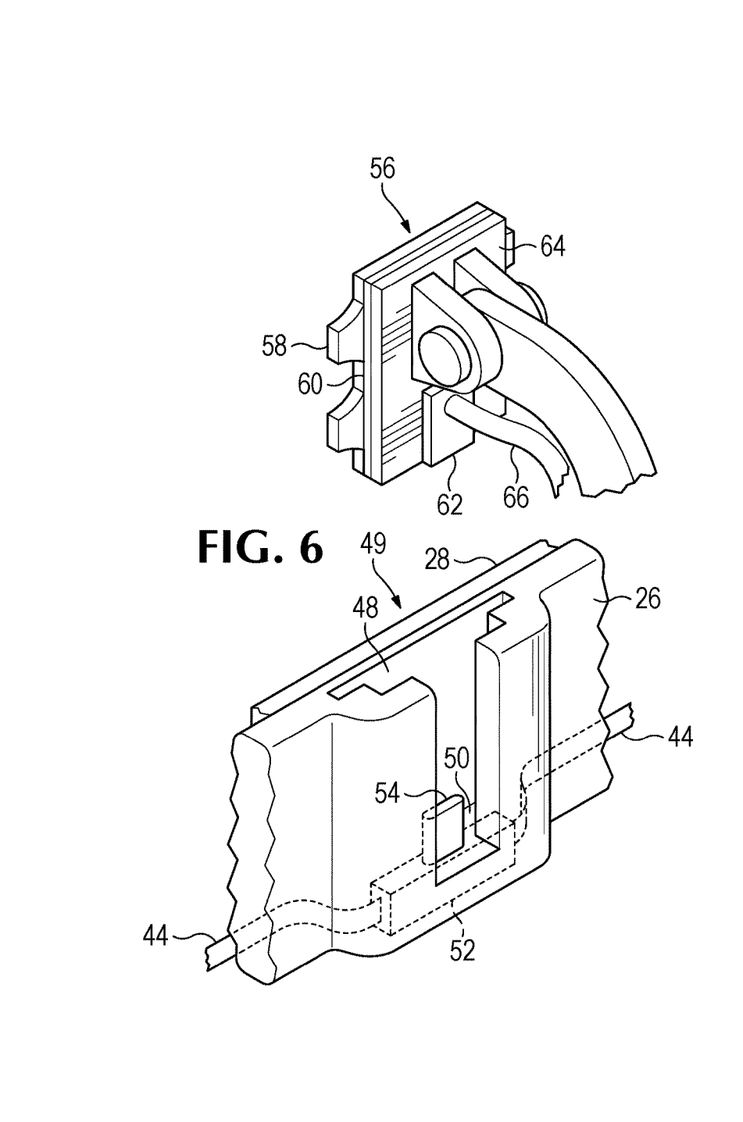
FIG. 6 is a partially disassembled view of the headlamp and headband connection area of FIG. 5.

Referring to FIGS. 5 and 6, a central portion 49, includes a portion of outer layer 26, which is formed with a centrally defined pocket 48, terminating at its lower end with an aperture 50. A flex circuit 44, from each side of assembly 10, both terminate in a block 52 set into a concavity defined in outer layer 26, which in turn terminates in a USB connector 54 that extends through aperture 50. From the top, a central layered structure 56 (FIG. 7) is lowered into pocket 48.

Figure 7:
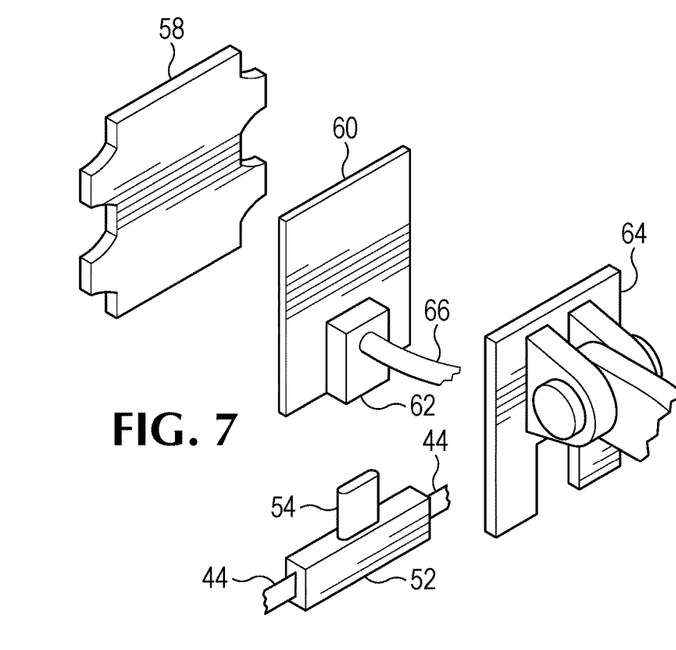
FIG. 7 is an exploded view of a portion of the headlamp and headband connection area of FIG. 5.
Figure 8:
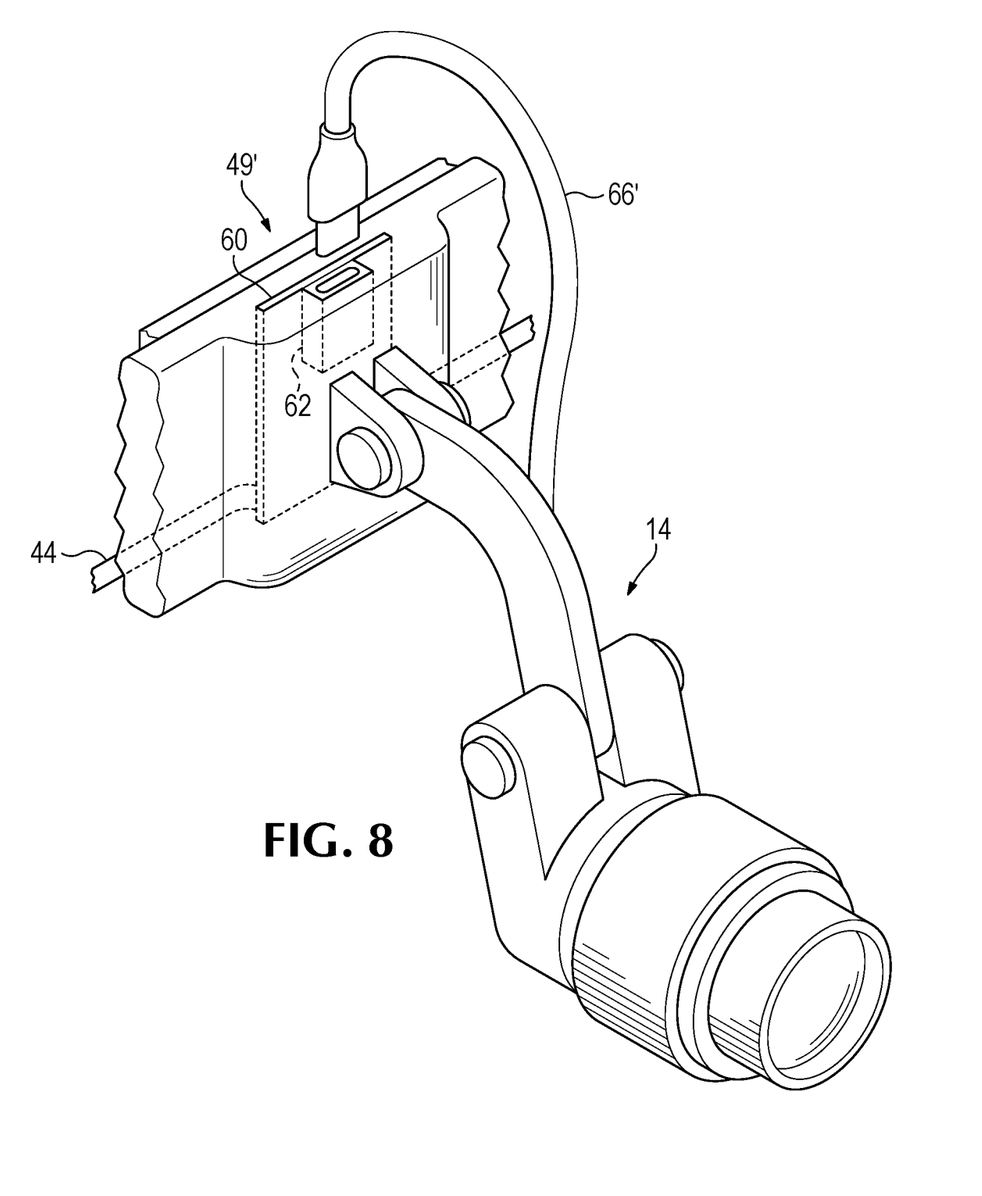
FIG. 8 is an isometric detail view of an alternative embodiment of the headlamp and headband connection area of FIG. 5, showing a different scheme of electrical connection.

Referring to FIG. 7, a stack structure 56 includes a back plate 58, a circuit board 60, which includes a USB port 62, which mates with connector 54, and a hinge plate 64, which supports headlamp sub-assembly 14. An outgoing cable 66 supplies sub-assembly 14 with electrical power. FIG. 8 shows an alternative embodiment of a central portion 49', in which cable 66 is replaced by a cable 66' terminating in a USB connector, thereby permitting easy replacement of subassembly 14. In an alternative to the embodiment of FIG. 8, there is a slot in the front of headstrap 16, so that structure 56 can be slid out of headstrap 16, with linkage and headlamp assembly 14 attached, as is the case for the assembly of FIG. 5. The remove-ability of sub-assembly 14 (FIGS. 1, 5, and 8) permits a detachment, if either headstrap sub-assembly 12 (FIG. 1) is malfunctioning or sub-assembly 14 is malfunctioning, but also permits sub-assembly 14, together with structure 56, to be inserted into a waiting receptacle of a helmet, such as those used in orthopedic surgery to protect the surgeon from flying bone shards, or glasses, that may serve both as eye-protectors and vision enhancers, in surgery.

Circuit board 60 typically hosts an integrated circuit microprocessor (not shown) and a DC-to-DC convertor (not shown), taking the voltage input from batteries 30 and rendering it into a desired voltage, according to input from brightness control knob 42. In an alternative preferred embodiment, circuit board 60 also includes a movement detector, such as an assembly of three orthogonal accelerometers and/or a gyro meter. In one embodiment the motion detector output is connected to a pin or pins of the microprocessor, which is programmed to detect a swift movement. This permits motion brightness control. where, for example, a user may move his head rapidly to his left to brighten the output of lamp 14, and move his head rapidly to his right to dim the output. Many alternative schemes of translating head motion to brightness are possible. The motion detector may also be connected to a "wake-up" pin of the integrated circuit microprocessor, which when the microprocessor is in a sleep state, using less than 10 micro Amps of current, and there is a prespecified change of state on this wake-up pin, the microprocessor is activated and is ready to accept further input from other sources.

There are many advantages to the design of assembly 10. First, plate 64 supplies rigidity to headband 16 in the critical central region. A problem has been noted of the headlamp sub-assembly swaying back and forth as the wearer moves his head. This can be distracting, particularly during surgery. The rigidity supplied by the design of assembly 10, particularly by plate 58 greatly reduces this problem.

Also, when a headlamp assembly stops functioning properly, isolation of the underlying problem can be difficult in products in which everything is joined together and cannot be separated. In the embodiment of central portion 49, the combination of sub-assembly 14 and circuit board 60 can be easily unplugged from USB connector 54, and connected to a test fixture, also having a USB connector, for identification of problems (if any) free from any problems that might be introduced by the headstrap subassembly 12. Headstrap subassembly 12 may be similarly tested. In the embodiment of central portion 49', the headlamp sub-assembly is easily unplugged from circuit board 60, which in an embodiment, can also be easily separated from headstrap subassembly 12, more easily permitting an isolation of the problem, to one of the three separable parts. Also, in this embodiment, the part of the headband 16 which is hardest coincides with the general flat and hard front of the forehead, and it is where the stiffness does the most good, in terms of keeping the headlamp from swaying.

In one preferred embodiment, outer polymer portion 26 is made principally of polypropylene. In an alternative preferred embodiment, outer portion 26 is made primarily of nylon. In preferred embodiments, outer polymer portion 26 has a Shore D durometer rating of greater than 45 (first embodiment), greater than 55 (second embodiment), greater than 65 (third embodiment), greater than 75 (fourth embodiment) and greater than 85 (fifth embodiment). In another preferred embodiment, outer polymer portion (26) has a Rockwell R rating greater than 110. The harder polymer of outer portion 26 provides greater stability for headlamp subassembly 14. Adding to the appearance of headlamp subassembly (14), and in embodiments, further enhancing stability, is a sock. The inner portion 28 is made of a softer polymer, such as polyurethane, for maximum wearing comfort.

In a further aspect of the present invention, in one embodiment the headstrap (16) is further thermoformed, so that it is shaped to fit onto a head, after initial forming. In one embodiment, the headband 16 is customized to the head of an intended wearer. The intended wearer has his head measured, and a shape is formed matching the shape of the intended wearer's head, with the headband 16 then wrapped about this shape and heated, to assume a shape adapted to be worn very comfortably by that wearer. In an additional innovation, an RFID chip is included in circuit board 60 (or elsewhere), and a signaling device, such as a speaker is provided. In the embodiment in which the headband 16 is customized, it becomes important to be able to quickly distinguish it from other headbands. This is done by decorating the headband 16 with a different visual pattern or by having the RFID chip and speaker so that a user may search for the customized headband using and RFID interrogation device and receive a "beep" in reply (or some other signal), such as an indication on the RFID interrogation device, leading him to the correct assembly 10. A sock 70 (Not Pictured) may be fit over a portion of sub-assembly 14, for aesthetic purposes, or to add stiffness, or both.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A medical headlamp assembly, comprising:
   a. a headstrap subassembly adapted to fit in a preferred orientation on a human wearer's head, and including a battery and a conductor extending from the battery to a front-center position, relative to said wearer's head when said headstrap is in said preferred orientation;
   b. a headlamp subassembly connected to and supported by the headstrap subassembly at said front center position, including a headlamp and a linkage, connected to the front center position and supporting the headlamp;
   c. a user input mechanism, permitting a user to indicate a desired brightness from the headlamp;
   d. a circuit board, positioned at the front center position of the headstrap subassembly, being no greater than 5 cm in width, and electrically connected to the conductor and to the headlamp, and including an integrated circuit implementing a DC-to-DC convertor supplying power to the headlamp, from the conductor, the power varying in accordance with said user input mechanism and;
   e. wherein said circuit board lends rigidity to said front center position, thereby helping to lessen side-to-side wobble of said headlamp subassembly.

2. The medical headlamp assembly of claim 1, wherein said user input mechanism is an actuator present on said headstrap subassembly, capable of movement in either of two directions, and communicatively connected to said integrated circuit, and wherein moving said actuator causes a signal to be sent to said integrated circuit directing either that increased or a decreased power be sent to the headlamp subassembly depending on direction said actuator movement.

3. The medical headlamp assembly of claim 2, wherein said actuator is a knob.

4. The medical headlamp assembly of claim 1, further including a rigid plate, positioned behind said circuit board on said headstrap.

5. The medical headlamp assembly of claim 1, wherein said headlamp subassembly and said circuit board are joined together and are removable, as a unit, from said headstrap subassembly.

6. The medical headlamp assembly of claim 5, wherein said circuit board is detachable from said headlamp subassembly.

7. The medical headstrap subassembly of claim 1, wherein said headband assembly and said circuit board are joined together and said headlamp subassembly is removeable from said joined headband assembly and circuit board.

* * * * *